United States Patent [19]
Hefner et al.

[11] Patent Number: 6,090,977
[45] Date of Patent: *Jul. 18, 2000

[54] CONTINUOUS HETEROGENEOUSLY CATALYZED GAS-PHASE PARTIAL OXIDATION OF AN ORGANIC COMPOUND

[75] Inventors: Werner Hefner, Lampertheim; Otto Machhammer, Kirchheim; Hans-Peter Neumann, Ludwigshafen; Andreas Tenten, Maikammer; Wilhelm Ruppel, Frankenthal; Herbert Vogel, Ludwigshafen, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/610,888

[22] Filed: Mar. 5, 1996

[30] Foreign Application Priority Data

Mar. 10, 1995 [DE] Germany ............................... 19508531
Jul. 13, 1995 [DE] Germany ............................... 19525505

[51] Int. Cl.$^7$ .................................................. C07C 27/14
[52] U.S. Cl. ...................... 562/512.2; 562/546; 562/547; 562/532; 562/545; 562/523; 562/534; 562/535; 562/542; 568/469.9; 568/479; 431/5
[58] Field of Search ................................ 562/512.2, 542, 562/546, 547, 549, 534, 535, 523; 568/469.9, 470, 476, 477, 478, 479, 480, 481, 482, 579, 657; 431/5, 7; 252/373; 423/418.2, 650; 585/539, 540, 538

[56] References Cited

U.S. PATENT DOCUMENTS

| | | | |
|---|---|---|---|
| 2,767,233 | 10/1956 | Mullen et al. | 585/541 |
| 3,692,823 | 9/1972 | Gordon | 260/497 A |
| 3,920,579 | 11/1975 | Slater | 252/373 |
| 4,031,135 | 6/1977 | Engelbach et al. | 562/535 |
| 5,684,188 | 11/1997 | Hefner et al. | 562/532 |

FOREIGN PATENT DOCUMENTS

| | | |
|---|---|---|
| 0 117 146 | 8/1984 | European Pat. Off. . |
| 0 128 404 | 12/1984 | European Pat. Off. . |
| 0 343 991 | 11/1989 | European Pat. Off. . |
| 2 097 476 | 11/1982 | United Kingdom . |
| WO 92/03213 | 3/1992 | WIPO . |

*Primary Examiner*—Rosalynd Keys
*Assistant Examiner*—Johann Richter
*Attorney, Agent, or Firm*—Oblon, Spivak, McClelland, Maier & Neustadt, P.C.

[57] ABSTRACT

In a process for the continuous heterogeneously catalyzed gas-phase partial oxidation of an organic compound in an oxidation reactor, whose feed gas mixture comprises, apart from the organic compound to be partially oxidized and molecular oxygen as oxidant, at least one diluent gas which is essentially inert under the conditions of the heterogeneously catalyzed gas-phase partial oxidation, where the essentially inert diluent gas consists partly of combustible gases, after passage through the oxidation reactor, the combustible constituents of the inert diluent gas present in the product gas stream leaving the oxidation reactor are not recirculated to the heterogeneously catalyzed gas-phase partial oxidation, but are put to further use for the purposes of another chemical reaction.

12 Claims, No Drawings

CONTINUOUS HETEROGENEOUSLY CATALYZED GAS-PHASE PARTIAL OXIDATION OF AN ORGANIC COMPOUND

The present invention relates to a novel process for the continuous heterogeneously catalyzed gas-phase partial oxidation of an organic compound in an oxidation reactor, whose feed gas mixture comprises, apart from the organic compound to be partially oxidized and molecular oxygen as oxidant, at least one diluent gas which is essentially inert under the conditions of the heterogeneously catalyzed gas-phase partial oxidation, where the essentially inert diluent gas consists at least partly of combustible gases.

For the purposes of the present invention, a complete oxidation of an organic compound means that the organic compound is reacted under the action of molecular oxygen in such a way that all the carbon present in the organic compound is converted into oxides of carbon and all the hydrogen present in the organic compound is converted into oxides of hydrogen. All other reactions of an organic compound under the action of molecular oxygen are here referred to in summary as partial oxidations of an organic compound.

In particular, partial oxidations here mean those reactions of organic compounds under the action of molecular oxygen in which the organic compound to be partially oxidized contains, when the reaction is complete, at least one more oxygen atom in chemically bonded form than before the partial oxidation is carried out.

For the purposes of the present invention, a diluent gas which is essentially inert under the conditions of the heterogeneously catalyzed gas-phase partial oxidation is a diluent gas whose constituents remain unchanged to an extent of, considering each constituent individually, more than 95 mol %, preferably more than 98 mol %, under the conditions of the heterogeneously catalyzed gas-phase partial oxidation.

For the purposes of the present invention, combustible gases are compounds whose mixtures with air at an initial pressure of 1 bar and an initial temperature of from 50 to 100° C. have an upper and a lower explosive limit (ignition limit), with the determination of the explosive limits being based on a measurement in the standard apparatus as described by W. Berthold et al in Chem.-Ing. Tech. (1984) 56 No. 2, pp. 126–127.

Explosive limits are here the following limit values in accordance with DIN 51649:

In a mixture of air and a combustible gas, the velocity at which combustion (ignition, explosion) initiated by a local ignition source (eg. glowing platinum wire) spreads under prescribed initial conditions is dependent on the combustible gas content. It is greatest at a particular content. Both increasing or decreasing the combustible gas content reduces the combustion velocity, until finally the combustion reaction just no longer spreads from the ignition source at a lower and an upper limit value for the combustible gas content. These two limit values are the lower explosive limit and the upper explosive limit; the range of combustible gas content lying between them is the explosive region (ignition region). Gases whose corresponding mixtures with air are not capable of a combustion reaction spreading from an ignition source at any mixing ratio are non-combustible inert diluent gases.

Examples of combustible gas are $H_2$, $NH_3$, methane, ethane, propane, butane (n- and/or iso-), pentane (n-, iso- and/or neo-), propyne, CO, acetylene, ethylene, diethyl ether, hydrogen cyanide and hydrogen sulfide. Further examples are given in the table on page 1285 of Römpp Chemie Lexikon, Cm-G, Thieme Verlag, Stuttgart, 8th edition (1990). Examples of non-combustible gases are $CO_2$, $H_2O$, $N_2$ and all noble gases.

The degree to which a combustible gas displays inert behavior in respect of a particular heterogeneously catalyzed gas-phase partial oxidation and thus is suitable as combustible constituent of the essentially inert diluent gas to be used can be determined by those skilled in the art by means of a few preliminary experiments.

It is generally known that numerous basic chemicals can be produced by partial oxidation of various organic compounds with molecular oxygen. Examples which may be mentioned are the reaction of propylene to give acrolein and/or acrylic acid (cf., for example, DE-A-2 351 151), the reaction of tert-butanol, isobutene, iso-butane, isobutyraldehyde or the methyl ether of tert-butanol to give methacrolein and/or methacrylic acid (cf., for example, DE-A-2 526 238, EP-B-92 097, EP-B-58 927, DE-A-4 132 263, DE-A-4 132 684 and DE-A-4 022 212), the reaction of acrolein to give acrylic acid, the reaction of methacrolein to give methacrylic acid (cf., for example, DE-A-2 526 238), the reaction of o-xylene or naphthalene to give phthalic anhydride (cf., for example, EP-A 522871) and also the reaction of butadiene to give maleic anhydride (cf., for example, DE-A-2 106 796 and DE-A-1 624 921), the reaction of indanes to give, for example, anthraquinone (cf., for example, DE-A-2 025 430), the reaction of ethylene to give ethylene oxide (cf., for example, DE-B-1 254 137, DE-A-2 159 346, EP-A-372 972, WO-89/0710, DE-A-4 311 608 and Beyer, Lehrbuch der organischen Chemie, 17th edition (1973), Hirzel Verlag Stuttgart, p. 261), the reaction of butadiene to give vinyloxirane (cf., for example, U.S. Pat. No. 5 312 931), the reaction of propylene and/or acrolein to give acrylonitrile (cf., for example, DE-A-2 351 151), the reaction of iso-butene and/or methacrolein to give methacrylonitrile, the oxidative dehydrogenation of hydrocarbons (cf., for example, DE-A-2351151), etc.

It is also generally known from the above documents that partial oxidations of organic compounds using molecular oxygen as oxidant can be carried out particularly selectively in the gas phase over catalysts present in the solid aggregate state. The catalysts are particularly frequently oxide compositions or noble metals (eg. Ag). The catalytically active oxide composition can contain, apart from oxygen, only one other element or more than one other element (multielement oxide compositions). Particularly frequently, the catalytically active oxide compositions used are those comprising more than one metallic, in particular transition metal, element. These are referred to as multimetal oxide compositions. Multielement oxide compositions are usually not simple physical mixtures of oxides of the elemental constituents, but heterogeneous mixtures of complex polycompounds of these elements.

These heterogeneously catalyzed gas-phase partial oxidations are usually carried out at elevated temperature (in general a few hundred ° C., customarily from 100 to 600° C.). Since most heterogeneously catalyzed gas-phase partial oxidations are strongly exothermic, they are frequently advantageously carried out in a fluidized bed or in multitube fixed-bed reactors with a heat exchange medium being passed through the space surrounding the contact tubes. The working pressure (absolute pressure) in the heterogeneously catalyzed gas-phase partial oxidations can be below 1 atm, at 1 atm or above 1 atm. In general, it is from 1 to 10 atm. The target reaction occurs during the residence time of the reaction mixture in the catalyst charge through which it is passed.

Owing to the generally pronounced exothermic character of most heterogeneously catalyzed gas-phase partial oxidations of organic compounds with molecular oxygen, the reactants are usually diluted with a gas which is essentially inert under the conditions of the gas-phase catalytic partial oxidations.

On the other hand, for the purposes of a heterogeneously catalyzed gas-phase partial oxidation of an organic compound with molecular oxygen, there is particular interest in a high space-time yield of the desired target compound; ie. there is interest in making the proportion by volume of the reactants in the starting mixture which is fed to the oxidation reactor as high as possible.

Of particular importance here is the proportion by volume of the molecular oxygen used as oxidant in the feed gas, as explained below.

Thus, on the one hand with regard to the stoichiometry of the partial oxidation to the desired target compound, it is generally necessary to use the molecular oxygen employed as oxidant in at least stoichiometric or in superstoichiometric amounts (eg. to reoxidize the oxidic composition used as catalyst and to reduce carbon deposits).

On the other hand, the proportion by volume of the molecular oxygen used as oxidant in the feed gas mixture must, for safety reasons, be below the oxygen limit concentration.

The oxygen limit concentration is that percentage by volume of molecular oxygen in the feed gas mixture below which, regardless of the proportion by volume of the other constituents of the feed gas mixture, namely particularly the organic compound to be partially oxidized and the inert diluent gas, combustion of, for example, the organic compound (explosive) initiated by a local ignition source (for example local overheating or spark formation in the reactor) can no longer spread from the ignition source at the given pressure and temperature of the feed gas mixture.

Accordingly, the oxygen limit concentration of the feed gas mixture thus sets the maximum proportion by volume in the feed gas mixture of the organic compound to be partially oxidized and thus influences the achievable space-time yield of target product (cf. EP-A-257 565, p. 5, lines 36/37).

Of course, the oxygen limit concentration of the feed gas mixture is significantly influenced by the type of constituents of the feed gas mixture, which is why particularly importance is attached to the selection of the inert diluent gas (its composition) for a heterogeneously catalyzed gas-phase partial oxidation of an organic compound with molecular oxygen.

The classical methods for heterogeneously catalyzed gas-phase partial oxidation of an organic compound generally recommend the non-combustible gases steam and/or nitrogen as inert diluent gas to avoid the explosive region (cf., for example, DE-A3 006 894, page 6, line 21, DE-A-2 056 614, page 2, last two lines, U.S. Pat. No. 4 147 885, column 1, lines 20 to 35, DE-A-2 547 536, claim 1, DE-A-2 436 818, page 2, paragraph 3, DE-A-2 202 734, page 4, lines 18 to 22 and DE-B-2 009 172, column 4, lines 40 to 45, with DE-A-2 056 614 attributing the particular suitability of steam as inert diluent gas to its relatively high molar heat capacity (p. 4, paragraph 2, line 1), whereas DE-B-2 251 364 mentions the cost aspect in respect of the frequent use of nitrogen as inert diluent gas (air as source of the oxidant). DE-A-1 962 431 likewise relates to a process for the heterogeneously catalyzed gas-phase partial oxidation of an organic compound with molecular oxygen. As suitable inert diluent gases, DE-A-1 962 431 names the non-combustible gases nitrogen, steam and carbon dioxide and also the combustible saturated hydrocarbons. DE-A-1 962 431 contains no example in which a saturated hydrocarbon is used as an inert diluent gas constituent. The question of further use of the inert diluent gas constituents present in the product gas mixture is not addressed in DE-A-1 962 431.

DE-A-2 251 364 recommends, as inert diluent gas in a process for the heterogeneously catalyzed gas-phase partial oxidation of an organic compound, the non-combustible gas steam to which the non-combustible gas nitrogen or combustible saturated hydrocarbons such as methane, propane or butane can be added. DE-A-1 468 429 recommends, as inert diluent gases in a process for the heterogeneously catalyzed gas-phase partial oxidation of an organic compound, carbon dioxide, nitrogen, saturated hydrocarbons or steam, with steam being preferred.

Neither DE-A-2 251 364 nor DE-A-1 468 429 include an example in which a saturated hydrocarbon would have been used as combustible diluent gas constituent. The question of further utilization of the inert diluent gas constituents present in the product gas mixture is not addressed in the two abovementioned documents.

DE-A-3 006 894 likewise concerns the problems, in a process for the heterogeneously catalyzed gas-phase partial oxidation of an organic compound with molecular oxygen, of, on the one hand, preventing a runaway reaction and, on the other hand, achieving a productivity which is as high as possible (p. 2, lines 11 to 19). The solution it recommends is to feed in the feed gas mixture at low catalyst activity and subsequently to successively increase the catalyst activity along the reaction coordinate. As inert diluent gas, DE-A-3 006 894 nominates the non-combustible gases nitrogen, carbon dioxide and/or steam.

German Auslegeschrift 1 793 302 relates to a process for the heterogeneously catalyzed partial oxidation of an organic compound in which the inert diluent gas used is, after separation of the target product, the reaction off-gas containing carbon oxides and water vapor produced in the reaction, ie. essentially non-combustible gas.

DE-A-2 056 614 likewise addresses the problems of preventing explosion-like combustion processes in a heterogeneously catalyzed gas-phase partial oxidation of an organic compound (eg. p. 3, paragraph 2, last two lines). To avoid adverse effects of the preferred diluent gas steam, DE-A-2 056 614 recommends recirculating the reaction off-gases largely freed of condensable gases, with partial or complete replacement of the water vapor, to the oxidation reactor as inert diluent gases and at the same time feeding in the feed gas mixture at low catalyst activity and subsequently successively increasing the catalyst activity along the reaction coordinate. Since the oxidant "molecular oxygen", is fed in as a constituent of air, the effective inert diluent gases in the method of DE-A-2 056 614 are essentially the non-combustible gases nitrogen and carbon dioxide. In respect of the inert diluent gases used, the method of DE-A-2 436 818 essentially corresponds to that of DE-A-2 056 614. The same applies to U.S. Pat. No. 4 147 885.

DE-A-2 729 841 relates to a process for the heterogeneously catalyzed gas-phase partial oxidation of an organic compound which, owing to the use of a specific oxidation catalyst, makes it possible to use, in place of steam as inert diluent gas, an essentially non-combustible gas mixture of CO, $CO_2$, nitrogen and argon which is separated from the product gas mixture of the heterogeneously catalyzed partial oxidation and is recirculated to the feed gas mixture.

With regard to avoiding an explosion risk in a heterogeneously catalyzed gas-phase partial oxidation of an organic compound with molecular oxygen, EP-B-253 409 (cf., in particular, p. 5, first three lines) and EP-A-257 565 disclose the use of inert diluent gases which have a relatively high molar heat capacity $C_p$. In these documents, mixtures of non-combustible gases such as nitrogen, $CO_2$, $H_2O$ and combustible gases such as methane, ethane and propane are recommended as preferred, for example, on page 4, lines 47 ff of EP-B-253 409 and on p. 5, lines 26 ff of EP-A-257 565. However, apart from the gases specified, it is also possible for helium, argon, other saturated hydrocarbon gases, $N_2O$ and carbon monoxide to be additionally present. Only the mean molar heat capacity of the inert diluent gas is considered important to its action. Thus, in all examples, the inert diluent gas of the feed gas mixture comprises more than 55% by volume of $N_2$. Furthermore, EP-B-253 409 and EP-A-257 565 recommend recirculating, at least partially, the inert diluent gases present in the product mixture to the feed gas mixture. EP-A-361 372 contains essentially the same teachings as EP-B-253 409 and EP-A-257 565.

The British Patent No. 1 450 986 recommends, particularly because of its relatively high molar specific heat, the use of carbon dioxide as inert diluent gas for avoiding the danger of explosion.

EP-A-293 224 relates to a process for the heterogeneously catalyzed gas-phase partial oxidation of an organic compound, in which the use of a gas mixture containing carbon dioxide, steam and saturated hydrocarbons having from 1 to 5 carbon atoms is recommended to ensure that the process is carried out safely (p. 3, lines 9 and 20 of EP-A-293 224). EP-A-293 224 considers the presence of carbon oxides in relatively high concentrations (p. 3, line 57) and a relatively high molar heat capacity of the inert gas mixture (p. 3, line 47) as important for the effectiveness of the inert gas mixture recommended by EP-A-293 224. EP-A-293 224 considers a further advantage of the method it recommends to be the fact that the inert gas mixture to be used can be obtained in large part from the product gas mixture of the partial oxidation. In all examples, the inert gas mixture used in the feed gas mixture includes steam and $CO_2$ in a total amount of at least 15% by volume, based on the inert gas mixture.

EP-A-117 146 concerns a process for the heterogeneously catalyzed gas-phase partial oxidation of propylene to acrylic acid, where the propylene is produced by heterogeneously catalyzed dehydrogenation of propane. EP-A-117 146 presents it as a particular advantage that the product gas mixture of the propylene dehydrogenation can be transferred without intermediate treatment to the oxidation stage and the inert constituents can subsequently be recirculated to the propane dehydrogenation stage. Similarly, the feed gas mixture in all examples includes an inert diluent gas comprising more than 15% by volume of steam. EP-A-372 972 concerns a similar process for preparing acrylonitrile, ethylene oxide and propylene oxide.

U.S. Pat. No. 5 312 931 relates to a process for the heterogeneously catalyzed gas-phase partial oxidation of butadiene to 3,4-epoxy-1-butene. The inert diluent gas used is butane. The background for this is the particular suitability of a butane/butadiene liquid mixture for the absorptive separation of the 3,4-epoxy-1-butene from the reaction mixture of the gas-phase 10 partial oxidation. DE-B-1 254 137 relates to a process for the heterogeneously catalyzed gas-phase partial oxidation of ethylene to ethylene oxide. The inert diluent gas used is methane.

A disadvantage of the teachings of the prior art is that recommended inert diluent gases include ones containing combustible constituents or consisting exclusively of such constituents, but it is not recognized that the oxygen limit concentration of a feed gas mixture containing molecular oxygen, inert diluent gas and gaseous organic substance to be partially oxidized is determined less by the molar heat capacity $C_p$ than by the combustibility of the inert diluent gas. The latter facts are the result of intensive research work and, without laying claim to being correct, can presumably be attributed to the fact that combustion explosions are generally free-radical chain reactions. Apparently, a partial oxidation of an organic compound in an environment of combustibly inert diluent gas constituents makes possible increased oxygen limit concentrations because combustible inert diluent gas constituents, unlike non-combustible inert diluent gas constituents, have a particular ability of stopping free-radical chain reactions (presumably as a result of own radical formation). This means that the higher the proportion of combustible constituents in the inert diluent gas of the feed gas mixture, the more safely can a heterogeneously catalyzed gas-phase partial oxidation of an organic compound with molecular oxygen be carried out, even with relatively high proportions by volume of the reactants.

A further disadvantage of the processes of the prior art is that those whose inert diluent gas includes combustible constituents recommend recirculation of the inert diluent gases present in the product gas mixture to the reactor feed. This is a disadvantage insofar as, during the heterogeneously catalyzed gas-phase partial oxidation, non-combustible gases such as $H_2O$ and $CO_2$ are also produced as byproducts or are introduced into the process together with the oxidant molecular oxygen (eg. $N_2$ when air is used as source of the oxidant). If they are also recirculated, this results, in continuous operation, in a reduction in the combustible proportions of the inert diluent gas present in the feed gas mixture. If they are not recirculated, this requires a complicated separation process of the non-combustible inert diluent gases present in the product gas mixture from the combustible inert diluent gases present therein or, for example, the use of a pure $O_2$ source. In addition, recirculation of inert diluent gases is fundamentally not inexpensive both on the investment side and on the side of running operating costs. On the other hand, combustible diluent gas constituents, unlike non-combustible inert diluent gas constituents such as $CO_2$, $H_2O$ or $N_2$, represent useful materials whose once-only use in a simple passage through the oxidation reactor essentially excludes economical operation of a heterogeneously catalyzed gas-phase partial oxidation of an organic compound.

It is an object of the present invention to develop an improved process for the continuous heterogeneously catalyzed gas-phase partial oxidation of an organic compound in an oxidation reactor, whose feed gas mixture comprises, apart from the organic compound to be partially oxidized and molecular oxygen as oxidant, at least one diluent gas which is essentially inert under the conditions of the heterogeneously catalyzed gas-phase partial oxidation, where the essentially inert diluent gas consists at least partly of combustible gases, which process does not have the disadvantages of the processes of the prior art.

We have found that this object is achieved by a process for the continuous heterogeneously catalyzed gas-phase partial oxidation of an organic compound in an oxidation reactor, whose feed gas mixture comprises, apart from the organic compound to be partially oxidized and molecular oxygen as oxidant, at least one diluent gas which is essentially inert under the conditions of the heterogeneously catalyzed gas-phase partial oxidation, where the essentially inert diluent gas consists partly of combustible gases, wherein, after passage through the oxidation reactor, the combustible constituents of the inert diluent gas present in the product gas stream leaving the oxidation reactor are not recirculated to the heterogeneously catalyzed gas-phase partial oxidation, but are put to further use for the purposes of another chemical reaction.

A simple example of further use of the combustible constituents of the inert diluent gas is there being passed to a thermal power station where they can be burned for energy recovery in a manner known per se. If the combustible constituents of the inert diluent gas are hydrocarbons, these can also be further used in a manner known per se for producing synthesis gas or acetylene (cf., for example, DE-A 4422815). Another possible further use sequence is provided by the catalytic gas-phase oxidation of propylene to acrolein and/or acrylic acid in the presence of propane and methane as inert diluent gas mixture. Subsequent to the gas-phase oxidation of the propylene, the propane/methane mixture which is inert in respect of this first reaction can be fed to a further catalytic gas-phase oxidation stage in which the propane is partially oxidized in the presence of the methane as inert diluent gas to give acrolein and/or acrylic acid. The methane can then be fed, for example in a thermal power station, to energy-generating combustion (the selectively acting catalysts necessary for each stage are generally known; cf., for example, EP-A 608838, EP-A 609112 and EP-A 257565 or EP-B 253409).

The advantage of the process of the invention is, inter alia, based on the fact that the feedstock "combustible diluent gas constituent" is utilized twice for single input costs:

a) for dilution of the feed gas mixture of the gas-phase partial oxidation of an organic compound, b) for example, as fuel in a thermal power station, or as starting material for producing synthesis gas.

Based on the conventional input costs of fuels in a thermal power station, or of hydrocarbons as starting compounds for the production of synthesis gas, the use according to the invention of combustible inert diluent gas constituents is thus cost neutral. The method of operation according to the invention is therefore particularly advantageous for those heterogeneously catalyzed gas-phase partial oxidations whose essentially inert diluent gas of the feed gas mixture in continuous operation comprises more than 85% by volume, preferably at least 90% by volume, better at least 95% by volume, even better at least 97% by volume, advantageously at least 98% by volume, preferably at least 99% by volume and best 100% by volume, of exclusively combustible inert diluent gas constituents. Preferably, the inert diluent gas mixture of the feed gas mixture for the purposes of the process of the invention includes no steam.

Furthermore, the process of the invention is of particular advantage for those heterogeneously catalyzed gas-phase partial oxidations of an organic compound whose feed gas mixture consists only of molecular oxygen, the organic compound to be partially oxidized and the inert diluent gas. In contrast thereto, the feed gas mixture in nitrile preparation generally includes ammonia as a further reactant.

The process of the invention naturally favors, among the combustible diluent gas constituents, the multiatom (>2 atoms) constituents, in particular those made up of a plurality of carbon and hydrogen atoms, since these are capable of forming a plurality of free-radical fragments capable of recombination. Furthermore, it is favorable if the boiling point of the inert diluent gas constituents is significantly below room temperature (25° C.) at atmospheric pressure (1 bar). Particularly advantageous inert combustible diluent gas constituents are therefore methane, ethane, propane, butane (n- and/or iso-) and mixtures thereof. Preferably, the inert diluent gas of the feed gas mixture in the process of the invention comprises more than 85% by volume, preferably at least 90% by volume, better at least 95% by volume, even better at least 97% by volume, advantageously at least 98% by volume, preferably at least 99% by volume and best 100% by volume, of at least one of the abovementioned saturated hydrocarbons. Of particular advantage is the use of methane and/or propane as inert diluent gas constituents. However, it is of course also possible to use aromatic hydrocarbons as combustible inert diluent gases.

For the following heterogeneously catalyzed gas-phase partial oxidations, the following saturated hydrocarbons are particularly suitable for the purposes of the process of the invention as main inert diluent gas constituent:

| Organic compound to be partially oxidized | Target compound | Preferred diluent gas constituent |
| --- | --- | --- |
| Propylene | Acrolein | Propane |
| Propylene | Acrolein | Methane |
| Propylene | Acrylic acid | Propane |
| Propylene | Acrylic acid | Methane |
| Acrolein | Acrylic acid | Propane |
| Acrolein | Acrylic acid | Methane |
| Ethylene | Ethylene oxide | Ethane or Methane |
| Butadiene | Vinyloxirane | Butane or Methane |
| iso-Butene | Methacrolein | iso-Butane or Methane |
| iso-Butene | Methacrylic acid | iso-Butane or Methane |
| Methacrolein | Methacrylic acid | iso-Butane or Methane |

Preferably, the above hydrocarbons make up more than 85% by volume, preferably at least 90% by volume, better at least 95% by volume, even better at least 97% by volume, advantageously at least 98% by volume, preferably at least 99% by volume and best 100% by volume, of the inert diluent gas of the feed gas mixture of the respective heterogeneously catalyzed gas-phase partial oxidation with molecular oxygen. The above hydrocarbons are also preferred as inert diluent gases for the respective heterogeneously catalyzed gas-phase partial oxidation because, inter alia, either they display a particular degree of inertness or if they are not completely inert they are converted at least partially to the desired target product.

Indispensible for the purposes of the process of the invention is the separation of the target product from the product gas mixture leaving the oxidation reactor. In favorable cases, the residual gas mixture which remains can be fed directly to its further use (eg. to the thermal power station). Frequently, particularly when the process of the invention is carried out at low conversions for selectivity reasons, unreacted starting material and/or intermediate will, however, be likewise separated off beforehand and generally recirculated to the oxidation reactor. If necessary, non-combustible inert diluent gas constituents (even those which are only formed as byproducts in the course of the reaction) such as $N_2$, $CO_2$ or $H_2O$ can likewise be separated to the further use of the gas (eg. passing on to the thermal power station) and, for example, be discharged into the atmosphere, so that a gas mixture consisting essentially exclusively of the combustible constituents is fed to the further use (eg. to the thermal power station). Other byproducts can, if necessary be likewise separated off prior to the further use (eg. passing on to the thermal power station), for example less favorable combustible inert gases such as CO which can likewise be present as reaction byproducts in the product gas mixture. The above applies similarly to the production of synthesis gas (term for a gas mixture consisting mainly of CO and $H_2$ which is used as starting material for synthetic processes and can be matched in terms of the ratio of the individual components to the respective applications; starting materials are, in particular, hydrocarbons which are reacted with steam and air or with $CO_2$ at relatively high temperatures (cf., for example, EP-A-533231)).

The separation processes to be used for this purpose, such as fractional condensation or absorption and extraction processes, are known to those skilled in the art and require no further explanation. The work-up and separation of the desired target product is likewise carried out in a manner known per se.

As source of the molecular oxygen required as oxidant for the purposes of the process of the invention, air has only limited suitability, since molecular oxygen occurs in air only in association with the non-combustible inert gas $N_2$. This means that the oxygen required for the process of the invention is preferably taken from an essentially pure oxygen source.

The process of the invention is particularly suitable for the preparation by gas-phase catalytic oxidation of acrolein, acrylic acid or a mixture thereof from propylene in a tube-bundle fixed-bed reactor charged with multimetal oxide catalysts. This is especially true since methane (which is particularly inert in respect of this reaction) as inert diluent gas of the feed gas mixture for the above reaction is at the same time particularly suitable for avoiding local overheating (hot spots) along the reaction tubes. As those skilled in the art generally know, the gas-phase catalytic oxidation of propylene to acrylic acid with molecular oxygen proceeds in principle in two successive steps along the reaction coordinate, of which the first leads to acrolein and the second leads from acrolein to acrylic acid. Accordingly, suitability of the process of the invention for the preparation by gas-phase catalytic oxidation of acrylic acid from propylene automatically includes suitability for the preparation by gas-phase catalytic oxidation of acrolein from propylene, since the acrylic acid preparation can at any time be interrupted at the acrolein stage. Furthermore, the reaction proceeding in two temporally successive steps makes it possible to carry out the preparation by gas-phase catalytic oxidation of acrylic acid from propylene in two successive oxidation stages, where, in each of the two oxidation stages, the oxidic catalyst to be used in each of the two oxidation stages can be optimized for the respective stage. Thus, for the first oxidation stage (propylene→acrolein) preference is generally given to a catalyst based on multimetal oxides containing the element combination Mo-Bi-Fe, while for the second oxidation stage (acrolein→acrylic acid) preference is normally given to catalysts based on multimetal oxides containing the element combination Mo-V. Appropriate multimetal oxide catalysts for the two oxidation stages have been described many times and are well known to those skilled in the art. For example, page 5 of EP-A-253 409 refers to appropriate U.S. patents. Useful catalysts are also disclosed by DE-A-44 31 957 and DE-A 4431949, particularly in the form of the multimetal oxide compositions of the general formula I. In general, the product mixture of the first oxidation stage is transferred without intermediate treatment to the second oxidation stage. The simplest embodiment of the two oxidation stages is therefore a tube-bundle reactor within which the catalyst charge changes appropriately along the individual contact tubes with completion of the first reaction step.

However, the two oxidation stages can also be carried out in an oxidation reactor comprising two oxidation reactors in series. In this case, the other reaction conditions, eg. the reaction temperature, can also be optimized in a simple manner in the respective oxidation stage. The molecular oxygen required for the second oxidation stage is here advantageously fed only to the second oxidation reactor. However, the heterogeneously catalyzed gas-phase partial oxidation of propylene to acrylic acid can in principle also be carried out in a single stage. In this case, both reaction steps occur in one oxidation reactor which is charged with a catalyst and catalyzes both reaction steps. of course it is also possible for the catalyst charge to change continuously or abruptly along the reaction coordinate within one oxidation stage. For the heterogeneously catalyzed gas-phase oxidation of propylene to acrolein, the propylene/molecular oxygen feed in the feed gas mixture preferably has a volume ratio of 1 (propylene): from 1 to 3 (molecular oxygen), preferably 1 (propylene): from 1.5 to 2 (molecular oxygen). The above propylene/molecular oxygen feed is advantageously also selected for the two-stage gas-phase oxidation of propylene to acrylic acid (eg. in an oxidation reactor comprising two oxidation reactors in series). In general, the product gas mixture leaving the first stage (the first oxidation reactor) is transferred without intermediate treatment to the second oxidation reactor. Advantageously, additional molecular oxygen as oxidant is fed to the second oxidation stage (the second oxidation reactor). The amount of molecular oxygen additionally fed in is preferably selected in such a way that the feed gas mixture of the second oxidation stage (the second oxidation reactor) also includes an amount of $O_2$ which is at least stoichiometric to about twice stoichiometric. For the first oxidation stage, the oxygen is here preferably likewise taken from an essentially pure oxygen source. If necessary, water vapor and $CO_2$ formed as byproducts in the first oxidation stage can be separated from the product gas mixture leaving the first oxidation stage (the first oxidation reactor) before it is transferred to the second oxidation stage (into the second oxidation reactor).

The difference between the process of the invention and the processes of the prior art is particularly that the process of the invention makes possible, in an economical way, an increased proportion of combustible constituents in the inert diluent gas of the feed gas mixture of continuous heterogeneously catalyzed gas-phase partial oxidations of organic compounds with molecular oxygen. This increased proportion of combustible constituents in the inert diluent gas of the feed gas mixture is, however, the prerequisite for safely carrying out heterogeneously catalyzed gas-phase partial oxidations or organic compounds, particularly those having increased proportions by volume of reactants in the feed gas mixture. The latter forms the basis for increased space-time yields. Thus, when using methane and/or propane as inert diluent gas of the feed gas mixture for the preparation of acrolein and/or acrylic acid, it is possible to handle with increased safety feed gas mixtures whose propylene feed is from >30% by volume to 40 or 45% by volume, based on the feed gas mixture. Favorable feed gas mixtures also include those which comprise:

from 15 to 30% by volume of propylene
from 20 to 40% by volume of oxygen and
from 30 to 65% by volume of methane and/or propane.
  Similar applies to the preparation of methacrolein and methacrylic acid. The process method of the invention is also particularly suitable for the preparation by gas-phase catalytic oxidation of phthalic anhydride, in particular from o-xylene.

EXAMPLES (influence of the combustibility of the inert diluent gas constituents on the oxygen limit concentration)

Determination of the oxygen limit concentration of feed gas mixtures at an initial temperature of 250° C. and an initial pressure of 1 bar and comprising propylene (organic compound to be partially oxidized), molecular oxygen (oxidant) and an inert diluent gas which is inert in respect of a heterogeneously catalyzed gas-phase partial oxidation of the propylene to acrylic acid.

General Experimental Procedure:

The experiments were carried out in a closed, spherical 5 l high-pressure vessel of stainless steel. The formation of the gas mixture in the initially evacuated high-pressure vessel was carried out by the partial pressure method. After mixing for 10 minutes by means of a magnetic stirrer, an attempt was made to ignite the gas mixture by means of a melting platinum wire. Any independent spreading of a reaction front (explosion) triggered thereby was detected by the rise with time of the internal pressure of the vessel (measured using a piezoelectric transducer) and by the increase in temperature in the vessel.

Results (the specific molar heat $C_p$ used are based on the data from "Ihsan Barin, Thermochemical Data of Pure Substances, Part I and Part II, VCH Verlagsgesellschaft, Weinheim, Second Edition, 1993", with ideal gas behavior being assumed for the gas mixtures):

a) Exclusive use of methane as inert combustible diluent gas, ie. the inert diluent gas consisted entirely of combustible constituents. The specific molar heat $C_p$ of methane is 47.5 J/mol·K under the specified conditions. The oxygen limit concentration determined is 32% by volume.

This means that, in a mixture of propylene, molecular $O_2$ and methane as inert gas, which is at 250° C. and 1 bar, a local ignition (explosion) can, regardless of the specific composition of the mixture, no longer spread independently when the proportion by volume of $O_2$ in the total gas mixture is <32% by volume, ie. in a mixture of 31% by volume of $O_2$, 20% by volume of propylene and 49% by volume of methane at 1 bar and 250° C., a local ignition can no longer spread independently.

b) Use of a 3.2 (propane): 96.8 ($CO_2$) mixture (ratio of the proportions by volume) of propane and carbon dioxide as inert diluent gas, ie. the inert diluent gas consisted virtually entirely of non-combustible diluent gas. The composition of the inert gas mixture was selected in such a way that it likewise has a $C_p$ of 47.5 J/mol·K under the specified conditions. The oxygen limit concentration determined is only 15% by volume. This means that in a mixture of 31% by volume of $O_2$, 20% by volume of propylene and 49% by volume of the inert diluent gas under conditions corresponding to a), a local ignition spreads independently.

c) Use of a 48.3 (propane): 51.7 (methane) mixture (ratio of the proportions by volume) of propane and methane as inert diluent gas, ie. the inert diluent gas consisted entirely of combustible constituents. The specific molar heat $C_p$ of this mixture is 80.8 J/mol·K under the specified conditions. The oxygen limit concentration determined is 37% by volume.

d) Use of a 50 (propane): 50 ($CO_2$) mixture (ratio of the proportions by volume) of propane and carbon dioxide as inert diluent gas, ie. the inert diluent gas also contained non-combustible constituents. The composition of the inert gas mixture was selected in such a way that it likewise has a $C_p$ of 80.8 J/mol·K under the specified conditions.

The oxygen limit concentration determined is only 34% by volume, ie. despite a significantly higher $C_p$ value for the inert diluent gas in comparison with a), the oxygen limit concentration is only a proportion by volume comparable with a).

We claim:

1. A process for the continuous heterogeneously catalyzed gas-phase partial oxidation of an organic compound in an oxidation reactor, comprising:

passing a feed gas mixture comprising (i) said organic compound to be partially oxidized, (ii) molecular oxygen as oxidant and (iii) at least one diluent gas containing more than 85% by volume of a combustible, saturated hydrocarbon which is essentially inert under the oxidation conditions, over a heterogenous catalyst in said reactor;

upon discharging a gaseous effluent from the reactor, separating and recovering the desired partially oxidized product from the gaseous effluent; and optionally separating and recycling unreacted organic compound and/or intermediates, which are oxidized in the reactor to product, to the reactor without recycling any other gaseous components of the gas discharged from the reactor, including said combustible, inert diluent gas(es), to the reactor.

2. The method as claimed in claim 1, wherein said oxidant is essentially pure oxygen.

3. The method as claimed in claim 1, wherein the organic compound to be oxidized is propylene, acrolein, ethylene, butadiene, i-butene or methacrolein.

4. The method as claimed in claim 1, wherein said at least one combustible inert gas diluent is methane, ethane, propane, i-butane or combinations thereof.

5. The method as claimed in claim 1, wherein said amount of combustible inert diluent gas is at least 90 vol. %.

6. The method as claimed in claim 5, wherein said amount of combustible inert diluent gas is at least 95 vol. %.

7. The process as claimed in claim 1, wherein the feed gas mixture for the oxidation reactor comprises propylene, molecular oxygen and a diluent gas comprising more than 85% by volume of at least one of the saturated hydrocarbons methane, ethane, propane and butane.

8. The process as claimed in claim 1, wherein the feed gas mixture sent to the oxidation reactor comprises 15 to 30 vol. % propylene, 20 to 40 vol. % of molecular oxygen and 30 to 65 vol. % of methane, propane or a combination thereof.

9. A process for fueling a thermal power station, comprising:

passing a feed gas mixture comprising (i) an organic compound to be partially oxidized, (ii) molecular oxygen as oxidant and (iii) at least one diluent gas containing more than 85% by volume of a combustible, saturated hydrocarbon which is essentially inert under the oxidation conditions, over a heterogenous catalyst in an oxidation reactor;

upon discharging a gaseous effluent from the reactor, separating and recovering the desired partially oxidized product from the discharged gaseous effluent;

optionally separating and recycling unreacted organic compound and/or intermediates, which are oxidized in the reactor to product, to the reactor without recycling any other gaseous components of the gas discharged from the reactor, including said combustible, inert diluent gas(es), to the reactor; and then passing the remainder of the gaseous effluent containing combustible constituents on to a thermal power station where they are burned for energy recovery.

10. The process as claimed in claim 9, wherein said combustible constituents of the remaining gaseous effluent of the oxidation reactor are separated from the gaseous effluent and are exclusively passed on to the thermal power station as a fuel.

11. A process for the continuous heterogeneously catalyzed gas phase partial oxidation of propylene to acrolein, acrylic acid or a mixture thereof, comprising:

passing a feed gas mixture comprising (i) propylene and (ii) molecular oxygen as oxidant in a volume ratio of 1:1–3 and (iii) at least one diluent gas containing more than 85% by volume of methane, propane or a combination thereof, which is essentially inert under the oxidation conditions over a heterogeneous catalyst in an oxidation reactor;

upon discharging the gaseous effluent from the reactor, separating and recovering the desired partially oxidized product of acrolein, acrylic acid or combination thereof, from the effluent gas; and optionally separating and recycling unreacted propylene to the reactor without recycling any other gaseous components of the gas discharged from the reactor, including methane and/or propane to the reactor.

12. A process for the continuous heterogeneously catalyzed gas-phase partial oxidation of an organic compound in an oxidation reactor, comprising:

passing a feed gas mixture comprising (i) from 15 to 30 vol. % of said organic compound to be partially oxidized, (ii) from 20 to 40 vol. % of molecular oxygen as oxidant and (iii) from 30 to 65 vol. % of at least one diluent gas containing more than 85% by volume of a combustible, saturated hydrocarbon which is essentially inert under the oxidation conditions, over a heterogenous catalyst in said reactor;

upon discharging a gaseous effluent from the reactor, separating and recovering the desired partially oxidized product from the gaseous effluent; and optionally separating and recycling unreacted organic compound and/or intermediates, which are oxidized in the reactor to product, to the reactor without recycling any other gaseous components of the gas discharged from the reactor, including said combustible, inert diluent gas(es), to the reactor.

* * * * *